United States Patent [19]

Alston, Jr. et al.

[11] 4,425,919
[45] Jan. 17, 1984

[54] TORQUE TRANSMITTING CATHETER APPARATUS

[75] Inventors: William W. Alston, Jr., Palo Alto; William G. Bloom, San Francisco; William C. Johnson, Menlo Park, all of Calif.

[73] Assignee: Raychem Corporation, Menlo Park, Calif.

[21] Appl. No.: 287,015

[22] Filed: Jul. 27, 1981

[51] Int. Cl.³ ............................................. A61M 25/00
[52] U.S. Cl. ................................... 128/658; 604/282; 138/124; 138/130
[58] Field of Search ............................ 128/348–350 R, 128/343, 656–658; 138/124, 125, 130, 132, 127; 428/36; 604/280, 282

[56] References Cited

U.S. PATENT DOCUMENTS

| | | | |
|---|---|---|---|
| 1,984,475 | 12/1934 | Goodall | 138/127 |
| 2,307,817 | 1/1943 | Austin | 428/36 |
| 2,962,050 | 11/1960 | Ramberg et al. | 138/127 X |
| 3,485,234 | 12/1969 | Stevens | 128/348 X |
| 3,924,632 | 12/1975 | Cook | 128/348 |
| 4,305,983 | 12/1981 | Hoppe et al. | 428/36 |
| 4,318,763 | 3/1982 | Bieler et al. | 428/36 X |
| 4,336,794 | 6/1982 | Chikama | 128/348 X |

*Primary Examiner*—Dalton L. Truluck
*Attorney, Agent, or Firm*—James W. Peterson

[57] ABSTRACT

A torque transmitting catheter apparatus including a longitudinally pre-oriented thin-walled tubular substrate surrounded by a thin-walled reinforcing means comprising a flat wire braid wound over the substrate and held in place by a thin-walled tubular superstrate surrounding the reinforcing means and in contact with the substrate through the reinforcing means.

9 Claims, 8 Drawing Figures

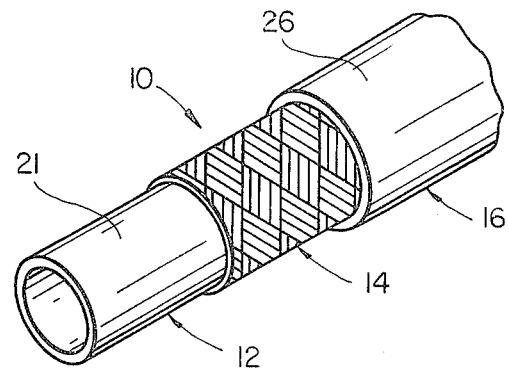
FIG_1
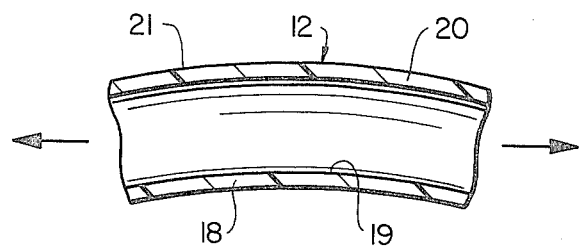
FIG_2
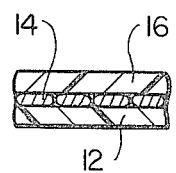
FIG_3A
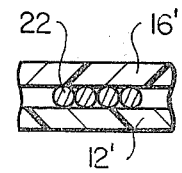
FIG_4A
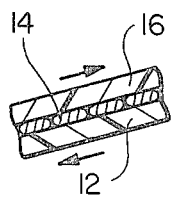
FIG_3B
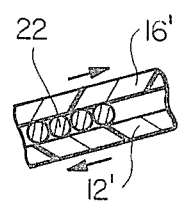
FIG_4B

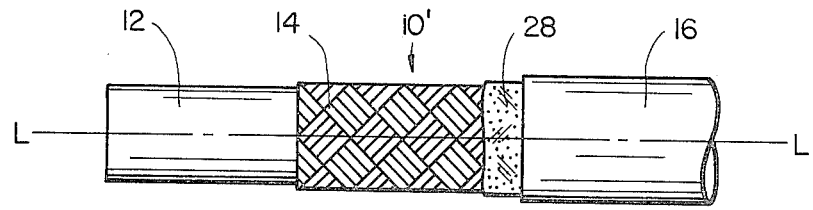
FIG_5
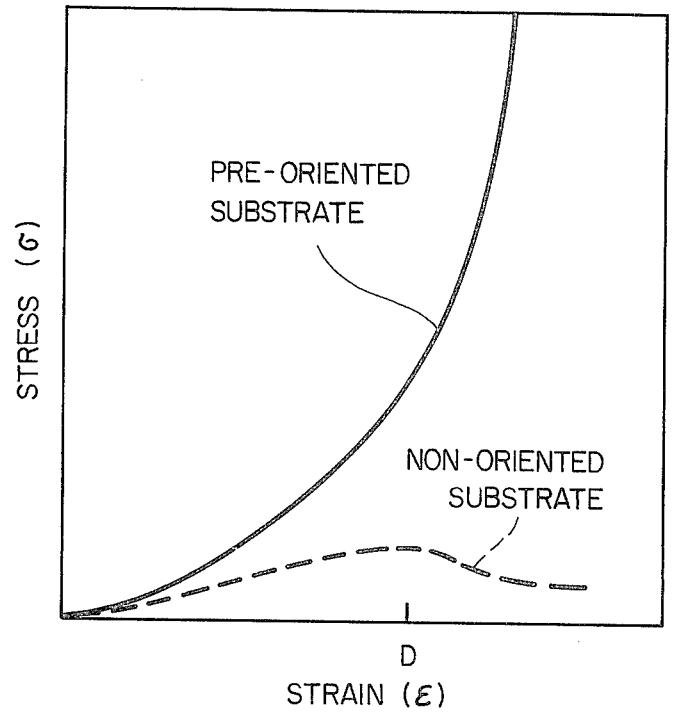
FIG_6

TORQUE TRANSMITTING CATHETER APPARATUS

BACKGROUND AND SUMMARY OF THE INVENTION

There have been many variations of catheter apparatus. A typical torque transmitting catheter apparatus is illustrated by Cook, U.S. Pat. No. 3,924,632, which includes several different layers bonded together. Cook discloses a catheter having a core, surrounded by a reinforcing layer, which is in turn surrounded by a superstrate or covering layer. In previous catheters, such as R. C. Steven, U.S. Pat. No. 3,485,234, the reinforcing layer consists of metallic braid of wire filaments which generally has a round cross section. The instant invention comprises a multi-element catheter apparatus which includes a special thin walled reinforcing means and special structure for supporting the reinforcing means which minimizes mechanical failure, while reducing the overall outside diameter of the catheter apparatus and yet providing adequate flow rate characteristics.

Catheterization procedures are used to diagnose the condition of a patient's body tissue such as arterial passageways or the like. Normally, an incision is made in the patient's body in order to insert the catheter apparatus into the passageways to be diagnosed. The catheter is then inserted through the incision and into the desired passageway. The catheter is fed through the passageway until it is correctly positioned adjacent the desired body organ, such as the heart. The catheter is then precisely rotated and manipulated into the desired body organ, for instance, the right coronary artery. Diagnostic fluid is then injected into the passageway at a predetermined minimum flow rate in order for a separate device, such as an x-ray, to properly record in photograph form the passageway. The physician may then properly diagnose the patient's condition.

The above described insertion process can induce trauma to the walls of the patient's passageways. In order to minimize the trauma, the instant invention may have a small overall outside diameter.

Trauma is further minimized by providing a highly flexible catheter which bends in conformance with the passageways. However, the catheter must be rigid enough to provide adequate torque transmission. Without sufficient torque transmission, the catheter cannot be precisely rotated into the desired body organ. Further, poor torque transmission causes buckling, wind-up and whiplash, inducing trauma to the passageways and causing pain and discomfort to the patient. Thus, heretofore the medical profession has been faced with a trade-off between a highly flexible catheter apparatus which fails to function adequately in torsion or a rigid catheter which creates an intolerable amount of trauma. The instant invention solves this dilemma by providing a thin wall reinforcing means comprising a flat wire braid wound over a longitudinally pre-oriented substrate which adequately supports the reinforcing means. The braid is maintained in place by a surrounding superstrate. Using this structure, the instant invention has extremely good torque transmission characteristics while maintaining superior flexibility. And, while the Cook patent, supra, discloses a flat braid of fiber glass it requires bonding to minimize kinking.

Because the instant invention includes a pre-oriented substrate, extremely thin walls are possible. This allows the overall outside diameter to be minimized while maximizing the inside diameter. This allows adequate diagnostic fluid to flow though the substrate thereby enabling the x-ray machine or the like to properly photograph the desired passageway.

The instant invention comprises a pre-oriented thin walled substrate, a thin wall reinforcing means and a superstrate which together cooperate and interact in a manner different than previously known to produce a flexible, small diameter, torque transmitting catheter which has adequate fluid flow characteristics and which functions according to generally accepted medical standards, while minimizing pain and discomfort to the patient.

OBJECTS OF THE INVENTION

The principal object of this invention is to provide a small outside diameter, highly flexible catheter which has excellent torque transmitting and fluid flow characteristics.

Another object of this invention is to provide a catheter apparatus which reduces the amount of trauma caused by feeding and rotating the apparatus during catheterization procedures.

Another object of this invention is to provide a thin walled catheter apparatus having a standard outside diameter while having greater than standard inside diameter, thereby having greater than standard flow rate characteristics.

Another object of this invention is to provide a catheter apparatus which includes a superstrate surface that is compatible with body tissue.

Another object of this invention is to provide a catheter having a substrate and superstrate which are strong enough to be thin walled while maintaining satisfactory torsional and strength characteristics.

Another object of this invention is to provide a catheter apparatus which includes a flat wire braid reinforcing means for maximizing torque transmission and to provide adequate support structure for minimizing kinking.

These and other objects of the invention described heretofore and hereinafter will become more clearly understood upon the description of the accompanying drawing wherein:

BRIEF DESCRIPTION OF THE DRAWING

FIG. 1 is a partially cut-away perspective view showing the basic elements of the catheter in accordance with this invention.

FIG. 2 is an enlarged longitudinal cross-sectional view of a portion of the substrate of FIG. 1.

FIG. 3A is a transverse section of the catheter in accordance with this invention. FIG. 3B is an illustration of the transverse section of the catheter of FIG. 3A after being subjected to torsional forces.

FIG. 4A is a transverse section of a catheter having a round wire reinforcing means. FIG. 4B is an example of a round wire reinforced catheter after being subjected to torsional forces.

FIG. 5 is a cut-away side view of an alternative catheter in accordance with this invention.

FIG. 6 illustrates the change in stress-strain relationship of the oriented substrate.

DETAILED DESCRIPTION OF THE INVENTION

With reference to the drawing wherein like reference characters designate like or corresponding parts throughout the several views, and with particular reference to FIG. 1, there is shown the catheter apparatus in accordance with this invention generally designated by the numeral 10.

The preferred embodiment of the instant invention includes a thin walled, pre-oriented tubular substrate 12 surrounded by a reinforcing means 14 tightly wound about its outside. The reinforcing means is in turn surrounded and pressed into further contact with the substrate 12 and maintained in that position by a superstrate 16.

The tubular substrate 12 is a special structure which is oriented by stretching in the longitudinal direction as indicated by the arrows of FIG. 2. In the preferred embodiment of the instant invention, the substrate is stretched between 100% and 500%. Using special materials, such as Nylon and particularly Nylon 12, it is possible to stretch the substrate greater than 500%. Orienting the substrate in this manner changes the substrates stress-strain characteristics which as will be explained more fully hereinafter, helps in preventing kinking.

The substrate as shown in FIG. 2 includes a thin inner wall 18 and a thin outer wall 20, with an inner surface 19 and an outer surface 21.

As can be seen in FIG. 2, when the substrate 12 is bent, such as when it goes through a twist or turn in a body passageway, the outer wall 20 is in tension while the inner wall 18 is in compression. The greater the tension forces, of course, the greater the compressive forces. As the bending force increases, a point is reached where very slight and unavoidable variations in the substrate wall thickness will lead to a sudden concentration of bending forces on a very small section of the substrate causing a collapse called a kink.

It is a well known physical fact that beyond a predetermined compressive force, slender columns are inherently unstable. As the catheter goes through certain body passageways, e.g. the aortic arch, it bends along a decreasing radius. The bending creates an increasing compressive force on the inner wall 18 of the substrate. Should the force increase beyond the predetermined force, the inner wall 18, analogous to a slender column in compression, will buckle causing a kink. This kink will be permanent since the elastic limit of the inside wall will have been exceeded.

The kink is unacceptable for two reasons. First, the kink causes at least a partial occlusion in the substrate preventing adequate diagnostic fluid from reaching the intended body tissue. Second, a weak spot is created in the structure of the catheter apparatus, which may burst under commonly used flow rates.

Using applicants' pre-oriented substrate, it has been discovered that as the compressive force increases during bending, the pre-oriented substrate increasingly resists further deformation. As can be seen in FIG. 6, the pre-oriented substrate has a different stress-strain curve than a substrate made from identical material but which is not oriented. As the strain on the pre-oriented substrate increases, the oriented substrate exhibits increasinly rapid changes in the stress. In mathematical form, the second derivative of the relationship between stress and strain is greater than 0, or as written mathematically, $(\partial^2\sigma/\partial\epsilon^2)>0$. The non-oriented substrate more quickly reaches its elastic limit and, more readily enters deformation as shown at point D. Further, and perhaps more importantly, the slope of the stress/strain curve of the non-oriented substrate decreases or is less than 0, which can be written as $(\partial^2\sigma/\partial\epsilon^2)<0$.

As explained earlier it is important to have a catheter with a small outside diameter but which still has adequate fluid flow characteristics. Therefore, it is desirable to have extremely thin walled substrates. However, a thin walled substrate under a bending force as described above, kinks more readily than does a thick walled one. Because the substrate 12 of the instant invention resists kinking to a greater degree than heretofore known, the wall may be extremely thin. In fact, the instant invention embodies a catheter having an overall outside diameter of approximately 0.100 inches (8 Fr.) with substrate wall thickneses as low as 0.005 inches, depending upon the materials used. Currently, polyvinylidene fluoride provides the best known results. However, Nylon 12 is also thought to be a good alternative.

In the preferred embodiment, the inner surface 19 is smooth so as to minimize friction on the flow of diagnostic fluid as it passes through the catheter apparatus. And the outer surface 21 should be strong enough to resist piercing by the reinforcing means 14.

The reinforcing means 14 comprises a flat wire braid as shown in FIG. 3. The flat wire braid reduces the overall diameter of the catheter as well as providing efficient torque transmission. By comparing FIG. 4A which shows a round wire braid 22 with FIG. 3A which shows the flat wire braid 14, it will be appreciated that the wall thickness of the flat wire is much less than the round wire. Additionally, as can be seen upon comparison between FIGS. 3A and 4A, the flat wire braid means 14 covers a greater portion of the substrate 12 as compared with the round wire braid 22 for the same number and gauge of wire filaments, The instant invention includes coverages of between 50% and 80% of the tubular substrate in the preferred embodiment.

The flat wire braid means 14 has the additional advantage of spreading the compressive force during torsional loading better than the round wire braid 22. As can be seen in FIG. 4B, the round wire braid is trapped between a tubular substrate 12' and surrounded by a tubular superstrate 16'. When the catheter of FIGS. 3B and 4B is torqued in the direction shown by the respective arrows, the compressive force is spread more uniformly on the substrate 12 because the flat wire braid resists rolling to a greater degree. In use, this resistance permits greater torsional loadings by maximizing the point at which wind up and whiplash occur. This aids the doctor in precisely rotating the instant invention to the desired body organ. However, the flat wire braid has the disadvantage of promoting kinking because it reduces the bonding area between the substrate and superstrate and reduces the overall wall thickness of the catheter. In typical embodiments of known catheter apparatus the elements are bonded together forming an integral, thick walled catheter. As discussed earlier, bonding is not required to minimize kinking in the instant invention because the substrate layer is pre-oriented. Using this structure, flat wire braid is practical. The instant invention further promotes torque transmission in the preferred embodiment by employing a braid with a particular braiding angle while still maintaining the preferred coverages of 50% to 80%. It has been found that flat wire braid such as 14 in FIG. 5 which has a braiding angle of between 35° and 60° with line L—L is preferred.

The preferred catheter of the instant invention includes a superstrate 16 which surrounds the tightly wound flat wire braid 14 and maintains said braid means 14 in intimate pressing contact with the substrate 12.

It may be preferable to make the superstrate 16 from cross-linkable material for sterilization purposes. Under accepted standards, exposing a material to radiation of 2.5. Mrads kills off bacteria and qualifies the material as sterilized. The preferred superstrate is a polymer selected from the group consisting of polyolefins. Alternatively, the superstrate may be made from ethyl vinyl acetate, and polyurethane.

The preferred superstrate may be made from cross-linkable material to allow flexibility in the formation of tips. Using the preferred superstrate, the doctor simply heats the tip, which is in one embodiment merely an extention of the superstrate, to its softening point and then forms the tip into its desired custom shape. In manufacturing a catheter with a tip of this type, one makes the length of the superstrate greater than ordinarily expected so that the extra length of superstrate extends beyond the reinforcing means and substrate. The catheter is cross-linked by radiation, for example. The catheter may then be heated beyond its softening point without melting and then formed into the desired tip shape. Of course, there are other methods of forming tips which could be readily adapted to the instant invention.

In FIG. 5 there is seen an alternative embodiment of the catheter apparatus in accordance with this invention generally designated by the numeral 10'. This embodiment includes the reinforcing means 14 impregnated with an adhesive 28 in order to bond the substrate 12 to the superstrate 16. This further encourages the superstrate 16 to hold the substrate 12 in place. Although the instant invention does not require such bonding, it has been found useful under certain circumstances. Additionally, it may be possible to bond the substrate and superstrate together by heating when the proper materials are selected.

While the instant invention has been described by reference to what is believed to be the most practical embodiments, it is understood that the invention may embody other specific forms not departing from the spirit of the central characteristics of the invention. It should be understood that there are other embodiments which possess the qualities and characteristics which would generally function in the same manner and should be considered within the scope of this invention. The present embodiments therefore should be considered in all respects as illustrative and not restrictive, the scope of the invention being limited solely to the appended claims rather than the foregoing description and all equivalents thereto being intended to be embraced therein.

What is claimed is:

1. A torque transmitting catheter apparatus for inserting diagnostic fluid into body tissue, the catheter being inserted into the body by a process of feeding and rotating the apparatus through body tissues such as arteries and the like body passageways, the apparatus comprising:
    a longitudinally pre-oriented thin-walled tubular substrate;
    a thin-walled reinforcing means surrounding and in contact with the substrate, the reinforcing means comprising a braid of flat wires wound over the substrate; and
    a thin-walled tubular superstrate surrounding the reinforcing means, and in contact with the substrate, forcing the reinforcing means against the substrate and maintaining the reinforcing means wound over the substrate.

2. The apparatus as set forth in claim 1 wherein the substrate is stretched between 300% and 500% in the longitudinal direction for pre-orientation.

3. The apparatus as set forth in claim 1 wherein the substrate is stretched greater than 500% in the longitudinal direction for pre-orientation.

4. The apparatus as set forth in claim 1 wherein the substrate and the superstrate are made from a cross-linkable material.

5. The apparatus as set forth in claim 1 wherein the substrate is made from polyvinylidene fluoride.

6. The apparatus as set forth in claim 1 wherein the substrate is made from Nylon 12.

7. The apparatus as set forth in claim 4 wherein the superstrate is irradiated at least 2.5 Mrad.

8. The apparatus as set forth in claim 1 wherein the reinforcing means comprises a flat wire braid covering the outer surface of the substrate between 50% and 80%.

9. The apparatus as set forth in claim 8 wherein the flat wire braid has a braiding angle of between 35° and 60°.

* * * * *